United States Patent

Pozzi et al.

(10) Patent No.: US 7,173,126 B2
(45) Date of Patent: Feb. 6, 2007

(54) CRYSTALLINE CEFDINIR SALTS

(75) Inventors: Giovanni Pozzi, Besana Brianza (IT); Patricio Martin Gomez, Salamanca (ES); Marco Alpegiani, Milan (IT); Walter Cabri, Rozzano (IT)

(73) Assignee: Antibioticos S.p.A., Rodano (IT)

( * ) Notice: Subject to any disclaimer, the term of this patent is extended or adjusted under 35 U.S.C. 154(b) by 0 days.

(21) Appl. No.: 10/539,122

(22) PCT Filed: Dec. 1, 2003

(86) PCT No.: PCT/EP03/13524

§ 371 (c)(1),
(2), (4) Date: Jun. 16, 2005

(87) PCT Pub. No.: WO2004/056835

PCT Pub. Date: Jul. 8, 2004

(65) Prior Publication Data

US 2006/0074236 A1    Apr. 6, 2006

(30) Foreign Application Priority Data

Dec. 20, 2002    (IT)    .................... MI2002A2724

(51) Int. Cl.
*C07D 501/22*    (2006.01)

(52) U.S. Cl. .................................... 540/222

(58) Field of Classification Search ............. 540/222
See application file for complete search history.

(56) References Cited

U.S. PATENT DOCUMENTS 6,350,869 B1 *    2/2002    Sturm et al. ............... 540/220
6,794,372 B2 *    9/2004    Del Soldato et al. ......... 514/81
2004/0210049 A1 *    10/2004    Lee et al. .................... 540/222
2006/0025586 A1 *    2/2006    Kremminger et al. ...... 540/222
2006/0040915 A1 *    2/2006    Kumar et al. ............... 514/202

FOREIGN PATENT DOCUMENTS

| EP | 0 304 019 A2 | 2/1989 |
| EP | 0 304 019 A3 | 2/1989 |
| GB | 1 392 536 | 4/1975 |
| WO | WO 02/098884 A1 | 12/2002 |
| WO | WO 2004/016623 A1 | 2/2004 |
| WO | WO 2006008160 A1 * | 1/2006 |

* cited by examiner

*Primary Examiner*—Mark L. Berch
(74) *Attorney, Agent, or Firm*—Rothwell, Figg, Ernst & Manbeck

(57) ABSTRACT

Cefdinir crystalline salts of formula (I),

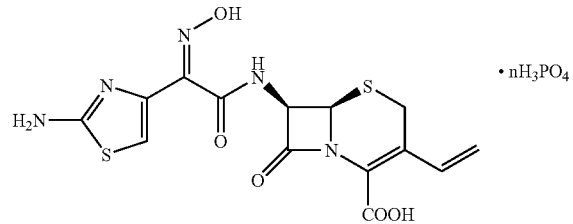

in which n ranges from 1 to 3, the preparation and use thereof for the preparation and purification of cefdinir are herein disclosed. The salts of formula (I) can be obtained from cefdinir intermediates or crude cefdinir by treatment with phosphoric acid.

9 Claims, No Drawings

CRYSTALLINE CEFDINIR SALTS

CROSS REFERENCE TO RELATED APPLICATION

This application is a 35 USC § 371 National Phase Entry Application from PCT/EP20031013524, filed Dec. 1, 2003, and designating the United States.

FIELD OF THE INVENTION

The present invention relates to crystalline cefdinir salts and to the process for the preparation thereof. These salts are useful intermediates in the synthesis and purification of cefdinir.

BACKGROUND OF THE INVENTION

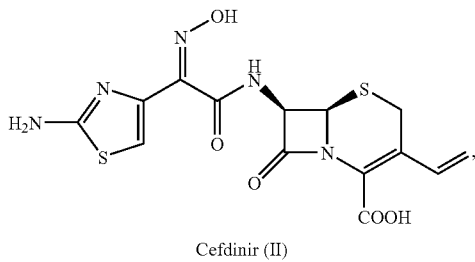

Cefdinir (II)

whose chemical name is [(−)-(6R,7R)]-7-{[(Z)-2-(2-aminothiazol-4-yl)-2-hydroxyiminoacetamido}-8-oxo-3-vinyl-5-thia-1-azabicyclo [4.2.0] oct-2-en-2-carboxylic acid, is a third generation semisynthetic cephalosporin for the oral use, characterized by a broad antibacterial activity spectrum and by antibiotic activity against gram-positive and gram-negative bacteria higher than that of other antibiotics for the oral administration. In particular, cefdinir shows an excellent antibacterial activity against staphylococci and streptococci.

Cefdinir is usually prepared through processes which envisage the protection of one or more of the primary amino, hydroxyimino or carboxy functions. The protective groups are removed at the end of the synthesis by means of acid hydrolysis.

U.S. Pat. No. 4,559,334 discloses a method for the preparation of cefdinir benzhydryl ester, which is hydrolysed with TFA in anisole or with $BF_3 \cdot Et_2O$.

WO 01/79211 teaches to prepare cefdinir via protection of the hydroxyimino and carboxy functions with a benzhydryl and a p-methoxybenzyl group respectively, which are subsequently removed with perchloric acid in an aprotic solvent and in the presence of an organic acid.

WO 97/24358 dicloses the preparation of a cefdinir salt with p-toluenesulfonic acid wherein the hydroxyimino function is protected with a trityl group.

Since cefdinir is poorly stable to acids, the aforementioned methods give sometimes unsatisfactory yields and the purity does not comply with the pharmacopoeia standards. The resulting product must therefore be subjected to further purification, for example to recrystallization (according to U.S. Pat. No. 4,935,507) or to formation of salts (according to U.S. Pat. No. 6,350,869).

DETAILED DISCLOSURE OF THE INVENTION

It has now been found that cefdinir salts of formula (I)

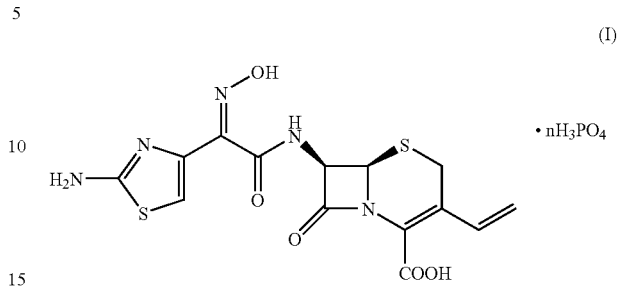

wherein n ranges from 1 to 3,
as well as hydrates and solvates thereof, allow to overcome the aforementioned drawbacks and are particularly useful intermediates in the preparation and purification of cefdinir.

Particularly preferred is the salt of formula (I) in which n is 2.

The salts of formula (I) are obtained by treating with phosphoric acid cefdinir protected forms of formula (III)

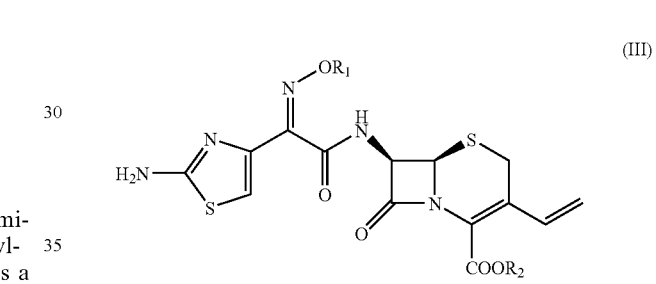

wherein
$R_1$ is a benzhydryl, trityl or p-methoxybenzyl group, and
$R_2$ is benzhydryl, t-butyl or p-methoxybenzyl group.

The reaction is carried out in a protic or aprotic, polar or a polar organic solvent, or in a mixture thereof. In more detail, the solvent is selected from nitriles, preferably acetonitrile or propionitrile; esters, preferably ethyl acetate, butyl acetate, ethyl formate and methyl acetate; amides, preferably N,N-dimethylformamide (DMF), N,N-dimethylacetamide (DMA), N-methylpyrrolidone (NMP); ketones, preferably acetone and methyl ethyl ketone; ethers, preferably tetrahydrofuran (THF) or dioxane; sulfoxides or sulfones, preferably dimethylsulfoxide (DMSO) and sulfolane; carboxylic acids, preferably formic and acetic acid; chlorinated solvents, preferably methylene chloride; and alcohols, preferably methanol, ethanol and isopropanol.

According to a particularly preferred embodiment of the invention, the solvent is acetonitrile.

Phosphoric acid is added, in the solid form or as an aqueous solution, in amounts ranging from 1 to 20 equivalents, preferably from 1 to 10 equivalents.

The reaction temperature ranges from −10° C. to 60° C., more preferably from 0° C. to 45° C.

The salts (I) usually crystallize in the reaction mixture and are recovered by filtration. To achieve complete precipitation, an organic solvent selected from the following can be added: nitriles, preferably acetonitrile or propionitrile; esters, preferably ethyl acetate, butyl acetate, ethyl formate and methyl acetate; ketones, preferably acetone and methyl ethyl ketone; ethers, preferably diethyl ether, diisopropyl ether and tert-butylmethyl ether.

The preparation of the salts (I) allows to simultaneously hydrolyse the protective groups and obtain cefdinir intermediates which are easily recoverable in the crystalline form, stable and highly pure (the purity is generally higher than 98%).

The salts (I) can be easily converted to cefdinir, or to a hydrated or solvated form thereof, by means of conventional methods, for example by treatment with an organic base, preferably a tertiary amine, more preferably triethylamine, or with an inorganic base, preferably ammonia, or carbonates, bicarbonates, hydroxides or phosphates of alkaline metals, preferably sodium or potassium, and optional treatment of the resulting salts with conventional acids. The reaction solvent can be water, or a mixture of water and alcohols, preferably methanol, ethanol, propanol or butanol; ketones, preferably acetone or methyl ethyl ketone, tetrahydrofuran or acetonitrile. The resulting solutions are treated with conventional acids; usually cefdinir precipitates as the solvate.

The salts of formula (I) are moreover particularly useful for the purification of crude cefdinir obtained by any other synthetic method. For this purpose, crude cefdinir is dissolved in water or in a protic or aprotic, polar organic solvent, or mixtures thereof, by addition of phosphoric acid, in the solid form or as an aqueous solution, in amounts ranging from 1 to 20 equivalents, preferably from 1 to 10 equivalents, at a temperature ranging from −10° C. to 60° C., preferably from 0 to 30° C. The organic solvent is selected from nitriles, preferably acetonitrile and propionitrile; amides, preferably N,N-dimethylformamide (DMF), N,N-dimethylacetamide (DMA) and N-methylpyrrolidone (NMP); ketones, preferably acetone; ethers, preferably tetrahydrofuran (THF); alcohols, preferably methyl, ethyl, propyl, isopropyl or n-butyl alcohol.

Usually, the salts (I) spontaneously crystallize from the reaction mixture, but crystallization can also be triggered and completed by addition of an organic solvent selected from those previously indicated for this purpose.

Once precipitation is complete, the salts (I) are recovered and converted to cefdinir as described above.

The invention is now illustrated by means of the following examples.

EXAMPLES

Example 1

7-(Z)-[2-(2-Aminothiazol-4-yl)-2-hydroxyiminoacetamido]-3-vinyl-3-cephem-4-carboxylic acid phosphate 100 Grams of 7-(Z)-[2-(2-aminothiazol-4-yl)-2-trityloxyiminoacetamido]-3-vinyl-3-cephem-4-carboxylic acid dicyclohexylamine salt was dissolved in a solution of 67 ml of 85% phosphoric acid in 1000 ml of acetonitrile. The mixture was heated at 45° C. for 2 hours, until complete conversion of the starting product (HPLC). After cooling to 20° C., the precipitate was filtered and washed with acetonitrile. After drying, 61 grams of cefdinir phosphate was obtained.

HPLC purity=98% (according to the method of the XIV Japanese pharmacopoeia)

$^1$H-NMR analysis confirmed the structure of the product, while $^{31}$P-NMR analysis confirmed the presence of phosphoric acid, which was also evident from the IR spectrum, showing characteristic bands at about 1115 and 970 cm$^{-1}$.

$^1$H-NMR (DMSO-d$_6$, 300 MHz): 11.27 (1H, broad s), 9.47 (2H, d, J=8.3 Hz), 7.13 (2H, broad s), 6.93 (1H, dd, J=17.5 Hz and 11.5 Hz), 6.68 (1H, s), 5.80 (1H, dd, J=8.3 Hz and 5 Hz), 5.60 (1H, d, J=17.5 Hz), 5.33 (1H, d, J=11.5 Hz), 5.20 (1H, d, J=5 Hz); 3.80 and 3.57 (2H, AB system, J=17.9 Hz).

Example 2

7-(Z)-[2-(2-Aminothiazol-4-yl)-2-hydroxyiminoacetamido]-3-vinyl-3-cephem-4-carboxylic acid phosphate 80 Grams of 7-(Z)-[2-(2-aminothiazol-4-yl)-2-trityloxyiminoacetamido]-3-vinyl-3-cephem-4-carboxylic acid was dissolved in a solution of 60 ml of 85% phosphoric acid in 1000 ml of acetonitrile. The mixture was heated at 45° C. for 2 hours until complete conversion of the starting product (HPLC). After cooling to 20° C., the product was filtered, washed with acetonitrile and dried. 61 Grams of cefdinir phosphate was obtained.

Example 3

7-(Z)-[2-(2-Aminothiazol-4-yl)-2-hydroxyiminoacetamido]-3-vinyl-3-cephem-4-carboxylic acid phosphate 10 Grams of 7-(Z)-[2-(2-aminothiazol-4-yl)-2-trityloxyiminoacetamido]-3-vinyl-3-cephem-4-carboxylic acid benzhydryl ester (prepared as reported in preparation A) is added to a solution of 21 ml of 85% phosphoric acid in 106 ml of acetonitrile. The mixture was heated at 45° C. for 6 hours, until complete conversion of the starting product (HPLC). After cooling to 20° C., the precipitate was filtered, washed with acetonitrile and dried. 2.8 Grams of cefdinir phosphate was obtained.

HPLC purity=99% (according to the method of the XIV Japanese pharmacopoeia).

Example 4

7-(Z)-[2-(2-Aminothiazol-4-yl)-2-hydroxyiminoacetamido]-3-vinyl-3-cephem-4-carboxylic acid phosphate 10 Grams of crude cefdinir (94% HPLC purity) (prepared according to WO 98/45299) was dissolved in 15 ml of 85% phosphoric acid and 15 ml of acetonitrile. The resulting solution was heated to 30° C. and cefdinir phosphate was crystallized by addition of 230 ml of acetonitrile. After cooling to 20° C., the precipitate was filtered, washed with acetonitrile and dried. 14 Grams of cefdinir phosphate was obtained.

HPLC purity~99% (according to the method of the XIV Japanese pharmacopoeia).

Example 5

7-(Z)-[2-(2-Aminothiazol-4-yl)-2-hydroxyiminoacetamido]-3-vinyl-3-cephem-4-carboxylic acid (cefdinir)

10 Grams of cefdinir phosphate was dissolved in 200 ml of water, adjusting the pH to 6 by addition of diluted ammonia at 5° C. and the solution was treated with active charcoal. After removal of the charcoal, the pH was adjusted to 2.5 by addition of diluted hydrochloric acid at 35° C. After 15 minutes the solution was cooled to 5° C. and the crystallized product was filtered, washed with water and dried. 6 Grams of cefdinir was obtained.

HPLC purity=99.5% (according to the method of the XIV Japanese pharmacopoeia)

$T_{(1\%, 510\ nm)}$=99.0% (test reported in U.S. Pat. No. 4,935,507)

Preparation A

7-(Z)-[2-(2-Aminothiazol-4-yl)-2-trityloxyiminoacetamido]-3-vinyl-3-cephem-4-carboxylic acid benzhydryl ester A suspension of 75 grains of 7-amino-3-vinyl-3-cephem-4-carboxylate benzhydryl hydrochloride in methylene chloride is treated under stirring with bis-trimethylsilylacetamide (90 ml) to obtain a clear solution. 60 Grams of 2-(Z)-(2-aminothiazol-4-yl)-2-trityloxyiminoacetic acid S-mercaptobenzothiazolyl ester is added and stirring is continued until completion of the reaction. The reaction mixture is poured in water (1 liter) and the phases are separated. The organic phase is dried over sodium sulfate and concentrated under vacuum. The residue is taken up with methylene chloride and methanol (1:1) under stirring. The solid is filtered and dried under vacuum to obtain about 105 g of product.

$^1$H-NMR (CDCl$_3$, 300 MHz): 7.2–7.5 (26H, m), 7.05 (1H, dd, J=17.6 Hz and 11.3 Hz), 6.99 (1H, s), 6.74 (1H, d, J=8.5 Hz), 6.67 (2H), 5.95 (1H, dd, J=8.5 Hz e 5.0 Hz), 5.44 (1H, d, J=17.9 Hz), 5.30 (1H, d, J=11.6 Hz), 5.07 (1H, d, J=5.0 Hz), 3.41 e 3.42 (2H, AB system, J$_{AB}$=17.6 Hz).

The invention claimed is:

1. Cefdinir salts of formula (I)

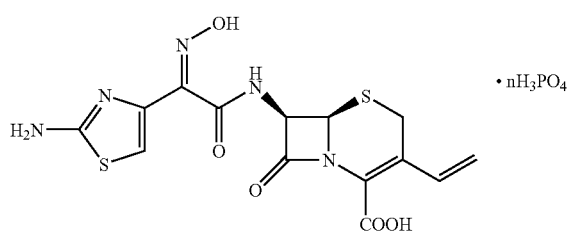

wherein n ranges from 1 to 3, and the hydrates and solvates thereof.

2. Cefdinir salt as claimed in claim 1 wherein n is 2.

3. Cefdinir salts according to claim 1 in the crystalline form.

4. A process for the preparation of salts of formula (I)

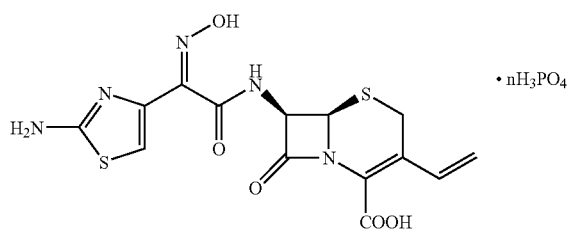

comprising treating with phosphoric acid a compound of formula (III)

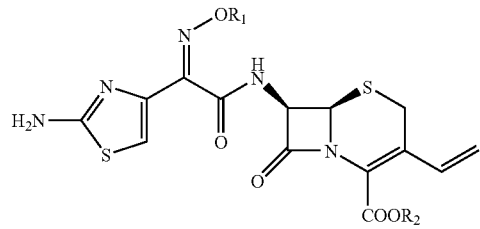

wherein
R$_1$ is a benzhydryl, trityl or p-methoxybenzyl group, and
R$_2$ is benzhydryl, t-butyl or p-methoxybenzyl group.

5. A process as claimed in claim 4 wherein the treatment is conducted in an organic solvent selected from: acetonitrile, propionitrile, ethyl acetate, butyl acetate, ethyl formate, methyl acetate, N,N-dimethylformamide (DMF), N,N-dimethylacetamide (DMA), N-methylpyrrolidone (NMP), acetone, methyl ethyl ketone, tetrahydrofuran (THF), dioxane, dimethylsulfoxide (DMSO), sulfolane, formic acid, acetic acid, methylene chloride, methanol, ethanol and isopropanol.

6. A process as claimed in claim 5 characterized in that the solvent is acetonitrile.

7. A process according to claim 4 characterized in that use is made of 1 to 20 equivalents of phosphoric acid.

8. A process for the preparation of cefdinir (II)

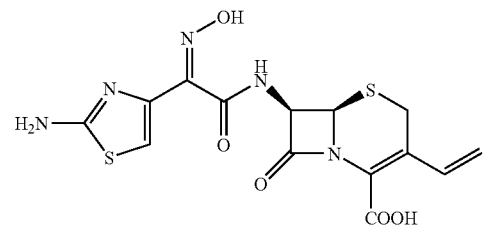

comprising treating salts of formula (I)

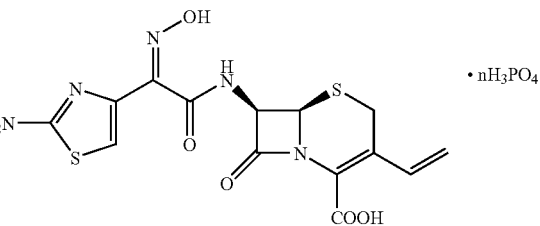

with an organic or inorganic base, in which the organic base is triethylamine and the inorganic base is ammonia, sodium carbonate or bicarbonate, or potassium hydroxide, followed by treating the resulting solution with conventional acids.

9. A process according to claim 8 wherein the salt of formula (I) is obtained by reacting crude cefdinir with phosphoric acid.

* * * * *